United States Patent [19]

Pickering

[11] 4,161,172

[45] Jul. 17, 1979

[54] LIFE SUPPORT CHAMBER FOR INFANTS, METHOD AND SYSTEM

[75] Inventor: Donald E. Pickering, Reno, Nev.

[73] Assignee: Airborne Life Support Systems, Inc., Reno, Nev.

[21] Appl. No.: 854,328

[22] Filed: Nov. 23, 1977

Related U.S. Application Data

[63] Continuation-in-part of Ser. No. 763,312, Jan. 28, 1977, Pat. No. 4,121,571.

[51] Int. Cl.² ........................................... A61G 11/00
[52] U.S. Cl. ........................................ 128/1 B; 128/172; 128/204; 128/400; 128/402; 362/379
[58] Field of Search ............... 128/1 B, 204, 400, 402, 128/399, 172, 191 A, 145 R, 297, 298, 1 R, 142.3, 30, 205, 185; 362/379

[56] References Cited

U.S. PATENT DOCUMENTS

| | | | |
|---|---|---|---|
| 1,688,200 | 10/1928 | Morgenthaler | 128/1 B |
| 1,739,641 | 12/1929 | Lessmann | 362/397 X |
| 2,353,536 | 7/1944 | Abbott et al. | 128/1 B |
| 3,338,233 | 8/1967 | Grosholz et al. | 128/1 B |
| 3,565,072 | 2/1971 | Gauthier | 128/191 A X |
| 3,593,712 | 7/1971 | Weaver | 128/191 A X |
| 3,858,570 | 1/1975 | Beld et al. | 128/1 B |
| 3,859,982 | 1/1975 | Dove | 128/298 X |
| 3,877,427 | 4/1975 | Alexern et al. | 128/1 B X |
| 3,885,571 | 5/1975 | Sachs | 128/191 A X |
| 4,003,378 | 1/1977 | Pickering | 128/1 B X |
| 4,034,740 | 7/1977 | Atherton et al. | 128/1 B |
| 4,079,728 | 3/1978 | Gatts | 128/1 B |

FOREIGN PATENT DOCUMENTS

| | | | |
|---|---|---|---|
| 285777 | 7/1967 | Australia | 128/1 B |
| 933727 | 9/1955 | Fed. Rep. of Germany | 128/1 R |
| 970939 | 11/1958 | Fed. Rep. of Germany | 128/1 B |

*Primary Examiner*—Henry J. Recla

[57] ABSTRACT

A box-like outer enclosure with flat clear rigid plastic walls forms an environmental chamber designed for a high-risk newborn infant. A flexible tubular membrane of clear plastic open at both ends optionally forms an inner enclosure for an infant within the chamber and is attachable at one end to an endwall of the chamber. A flat two-piece clear plastic lid slidable along the top edges of the outer enclosure's sidewalls provides top access to the chamber at its center and both ends. The lid is held in place without restricting its sliding movement by spring clamps. Legs on the outer enclosure elevate it above a supporting platform and are attachable to such platform. A breathable gas circuit including a heater with a fan forces a variable and humidified mixture of air and oxygen at a controlled temperature and flow rate into the chamber through an endwall intake opening provided with vertically oriented vanes. The gas is discharged from the chamber through an opposite endwall exhaust opening. If the inner membrane enclosure is used, the breathable gas is channeled through it at a laminar flow rate before being discharged into and finally exhausted from the chamber. A lamp within a suction cup attachable to the outer surfaces of the outer enclosure illuminates the chamber at night. Access to the chamber for tubing and monitoring wire leads are provided by small notches in the upper edges of the end walls of the outer enclosures. An infrared heating light is mounted above the enclosure for heating the outer surface of the inner membrane when the top lid is open.

8 Claims, 11 Drawing Figures

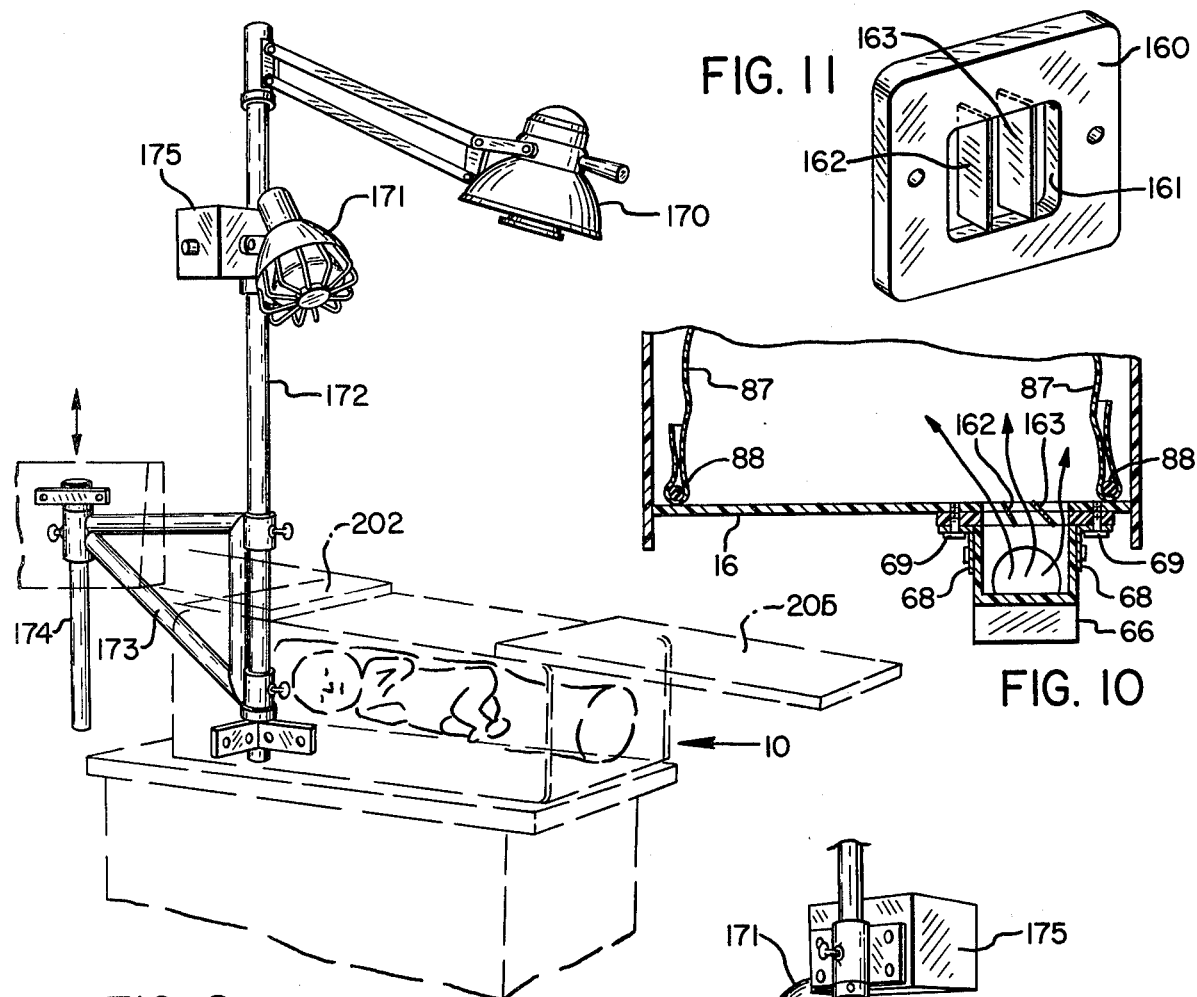
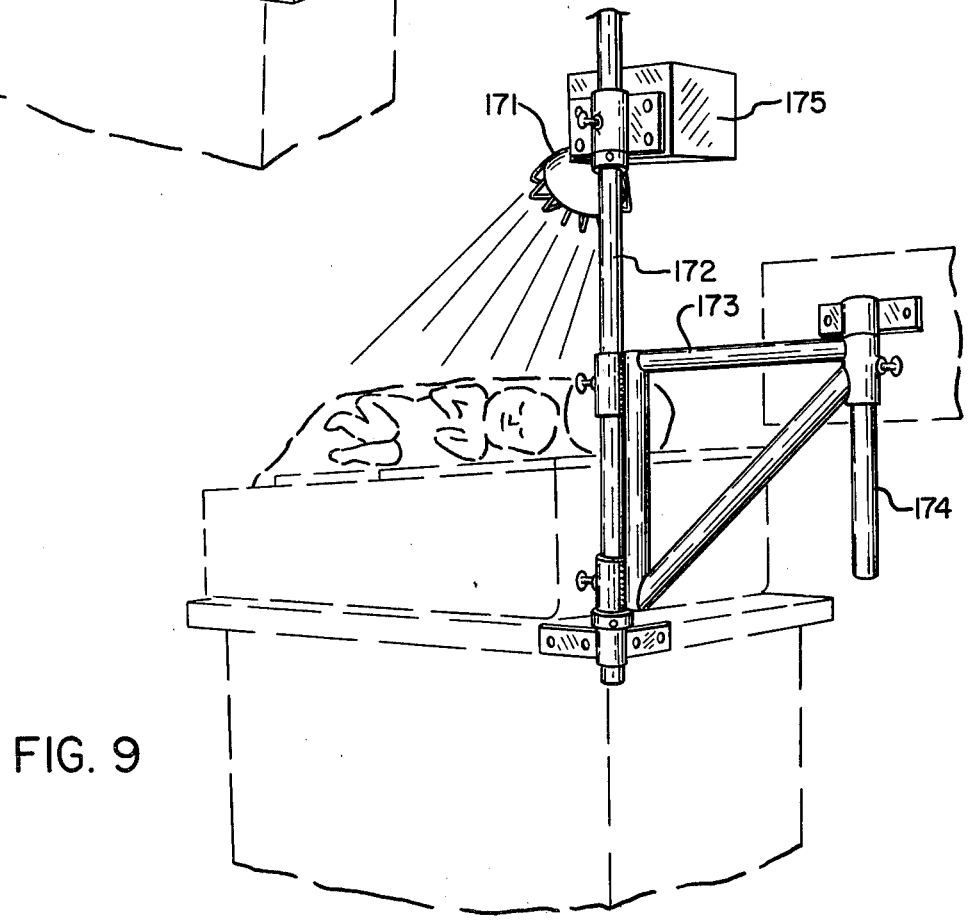

LIFE SUPPORT CHAMBER FOR INFANTS, METHOD AND SYSTEM

BACKGROUND OF THE INVENTION

CROSS REFERENCE TO RELATED APPLICATION

This application is a continuation-in-part of my co-pending application, Ser. No. 763,312, filed Jan. 28, 1977 now U.S. Pat. No. 4,121,571, "Transportable Life Support Chamber, Method and System."

FIELD OF THE INVENTION

The present invention relates to the maintenance of a stable, life-supporting environment for high-risk infants and others and especially to devices, methods and systems which can be used in both a stationary and a transport mode such as in hospitals, ambulances and aircraft.

DESCRIPTION OF THE PROBLEM AND PRIOR ART

High-risk newborn infants, particularly those with respiratory disease syndrome or other respiratory problems, demand a stable supportive environment, usually including one that is warm, oxygen rich, draft-free and humidified, to minimize the impact of the illness on their condition. The maintenance of such an environment during transport of the newborn is difficult at best. Especially in remote areas, high-risk infants must often be transported from a small community hospital over a distance of several hundred miles or more by aircraft or ambulance, or both, to a regional intensive care nursery. In such circumstances the maintenance of a protective, stable, supportive environment for the infant is particularly difficult, especially because it is often necessary to begin therapy and medical procedures during transport. The foregoing transport problems and recommended equipment, procedures and principles of transport are discussed in the book *Transport of High-Risk Newborn Infants—Principles, Policies, Equipment, Techniques,* published by the Canadian Pediatrics Society, in 1972. Also see in this regard Chapter 6, "Transportation of the High-Risk Infant", of the book *Care of High Risk Neonate,* by Klaus and Fanaroff.

Conservation or restoration of the high-risk infant's body heat is vital and a particular problem during transport. Hypothermia is a frequent complication and danger in high-risk newborn infants, and can be fatal. See, for example, "Stabilization and Transport of Severely Ill Infants", by Cunningham and Smith in Vol. 20, No. 2 (May 1973), issue of *Pediatric Clinics of North America.* See also in this regard Chapter 13, "The Respiratory Distress Syndrome of the Newborn", by George W. Brumley in the book *The Critically Ill Child,* by Clement A. Smith.

The importance of maintaining an adequate environmental temperature to prevent harmful heat loss in a newborn, and the consequences of not doing so, are discussed in Chapter 8, "Thermoregulation in the Newborn", by J. W. Scopes, of the book *Neonatology—Pathophysiology and Management of the Newborn,* published by J. B. Lippincott Company, and in some of the other aforementioned references. According to studies reported in the above Scopes reference, adequate environmental warmth alone tripled the chances of survival of very small newborn babies. The range of environmental temperature that the newborn can tolerate when naked in an incubator is very narrow and therefore must be controlled precisely. The difficulty of maintaining the required environmental temperature increases greatly during transport, especially if medical or surgical procedures must be administered.

Not only is it difficult to provide adequate warmth for the newborn, but even more difficult is the determination of the optimal thermal environment for the newborn, particularly one in the high-risk category. This, too, is discussed by Scopes in "Thermoregulation in the Newborn", supra, and by some of the other aforementioned references. A baby, like any physical body, exchanges heat by conduction, convection, evaporation and radiation. Babies in controlled environmental chambers, such as clinical warm air incubators, do not experience appreciable heat loss through conduction because they usually lie on a matress of low conductivity. The major channels of heat loss in infants at moderate temperatures are through convection and radiation. Scopes teaches that convective heat loss can be reduced by increasing the environmental air temperature and reducing air speed. However, a high environmental air temperature can result in high evaporative heat loss, but this can be counteracted by increasing the relative humidity of the environment and reducing air speed. Radiant heat loss from the infant depends on its presenting surface area and skin temperature as compared with the surface temperature of the receiving surface, usually the inside surface of the incubator canopy, which is usually pervious to thermal radiation. Thus thermal radiation represents a major source of heat loss from a naked infant in an incubator. Scopes suggests as a solution to the problem interposing a second layer of the rigid plastic canopy material between the baby and the outer canopy of the incubator, the inside surface of which will be warmed by the warm air of the incubator, thereby reducing appreciably radiant heat loss from the infant. He also suggests the possibility of using a radiant heat source directed into the incubator to counteract radiant heat loss from the incubator.

It is often necessary for the attending physician to begin therapy and medical procedures during transport in order to aid the high-risk newborn in its struggle to survive. Such procedures may include resuscitation and application of continuous positive airway pressure through endotracheal intubation. Other procedures may include endotracheal suction and intraveneous feeding. The infant's body temperature, blood pressure and pulse should be carefully monitored, which requires that wire leads extend from the monitoring equipment to sensor-transducers which are applied directly to the infant. See the discussion of some of these procedures in Chapter 1, "Resuscitation of the Newborn Infant", by Fischer and Behrman from *Care of the High Risk Neonate,* by Klaus and Fanaroff, and "Respiratory Care of Newborn Infants", by Gregory in Vol. 19, No. 2 (May 1971) of *Pediatric Clinics of North America,* and some of the previously mentioned references.

Ideally all of the foregoing procedures and others should be performed while the infant's environmental temperature, humidity, atmosphere and circulation remain stable at desired levels, a difficult task at best in a nursery setting, and even more difficult in a transport mode.

No prior known environmental chambers enable the maintenance of a stable supportive environment as aforesaid during infant transport and especially while administering procedures during transport. All known environmental chambers readily capable of transport are inadequate to achieve this ideal. For example, U.S. Pat. No. 3,858,570 discloses an environmental chamber having a domed hood with a built-in radiant heat source. However, such chamber is obviously unsuited, because of the supporting equipment on which its operation depends, for use in transporting an infant by ambulance or aircraft. It also provides no disclosed means for maintaining a controlled environmental temperature, humidity, airflow and air-oxygen mixture in the chamber, particularly during transport and while administering procedures to the infant. Other prior art chambers having some or all of the same inadequacies include those shown in U.S. Pat. No. 2,822,803; 3,889,670; 3,786,809; 3,335,713; 3,000,379; 2,776,657; and 2,699,775; German Pat. No. 164,163; and Belgian Pat. No. 510,199.

During the development of my present invention over the past several years, I have made and tested under actual operating conditions using newborn infants, both in the nursery and in ambulances and aircraft, various experimental prototype chambers, methods and systems. Such prototypes often exhibited some but not all of the advantages of the invention as disclosed herein. One such prototype was disclosed in the January, 1974, issue of "Our Temperature, Pulse and Respiration", a publication of the Washoe Medical Center in Reno, Nevada, where I am a practising physician.

In my prior copending patent application Ser. No. 516,119, filed Oct. 18, 1974, entitled "Transport and Life Support System for Infants", now U.S. Pat. No. 4,003,378, I disclose an infant life support hood and tray, the hood of which can be pressurized for maintaining a desired atmospheric pressure within the hood under varying ambient pressure conditions such as during transport by unpressurized aircraft or during ground transport at varying elevations. Such hood is also capable of maintaining a continuous positive airway pressure in the infant indirectly through pressurization of the hood chamber or directly using endotracheal intubation. The hood is constructed of a clear rigid plastic for protection and encloses at least the infant's head, neck and chest. A breathable gas is delivered to the hood chamber through small ports in the top of the hood which also has a small access port with a removable cover through which medical procedures can be administered. An infant is placed within the hood through an endwall opening having a flexible closure which must be bonded to the infant's body to create a pressure seal. Suction and IV tubing and wire leads for physiological monitoring transducers are passed through this opening also.

While satisfactory for its intended purpose, the foregoing prior hood does have drawbacks and is not the optimum infant life support chamber for several reasons. First, placement of the infant in the chamber and then sealing the chamber is too difficult and time consuming, and often an imperfect seal is formed. Second, no satisfactory means is provided for maintaining and circulating a desired life-sustaining atmosphere within the hood. Third, no satisfactory means is provided for maintaining a desired environmental and body temperature within the chamber. Fourth, access to the infant for administering procedures is too restricted and difficult. Fifth, visibility to the infant is somewhat impaired by the appurtenances on the top wall of the hood. Sixth, better access for monitoring wire and tubing leads is needed. Seventh, no ready means is provided for x-ray photography of the infant while in the hood. Eighth, the hood is not designed for compatibility with and securement to various stationary and transport platforms, and is not readily adaptable for use as part of an overall integrated stationary or transportable life support system. Ninth, the hood and tray combination does not optimally protect the infant during transport. Finally, it has been determined through experience that it may be undesirable under many circumstances to pressurize the hood chamber because of the serious and harmful consequences that can result through improper use or malfunction of the life-support equipment.

Accordingly, there is a distinct need for a transportable enviromental chamber capable of transporting a high-risk infant alternatively within the hospital or out of the hospital by aircraft or ambulance while maintaining a protective, stable supportive environment for the infant while at rest and during medical procedures.

Finally, there is a need for a life support chamber of the type described that can be used in-hospital, as, for example, in an intensive care unit, and that will maintain a protective, stable supportive environment for an infant in the high-risk category.

SUMMARY OF THE INVENTION

The present invention comprises a method and system for maintaining a stable supportive environment for a high-risk newborn infant and others. The method and system provide control of environmental temperature, humidity, environmental atmosphere, and atmospheric circulation while the infant is being transported or, alternatively, while he is in a hospital intensive care unit. The desired environment can be maintained both with the infant at rest and while medical personnel are administering procedures.

The invention also comprises an environmental chamber for the infant or others forming a part of the foregoing system and enabling performance of the foregoing method. The environmental chamber includes an inner clear flexible membrane enclosure for the infant which reduces radiant heat loss from the infant and channels a predetermined air-oxygen mixture to the infant at a desired flow rate, temperature and humidity.

Principal objectives of the invention include:

Providing a method and means for maintaining high-risk infants and others in a stable life-supportive environment during transport or in-hospital and with the patient either at rest or undergoing medical procedures;

Providing an environmental chamber for maintaining the aforesaid stable supportive environment, with such chamber being readily transportable both within a hospital and in ground and air transport vehicles and readily usable with various mobile and stationary life support platforms;

Providing ease of access to all portions of the patient for performing procedures while maintaining the aforesaid stable supportive environment;

Providing optimum visibility of the patient while in the aforesaid stable, supportive environment, even in ambient darkness;

Providing a stable supportive environment as aforesaid which can be regulated with respect to environmental temperature, humidity, oxygen content and atmospheric flow rate to protect the patient against possibly injurious heat loss or gain and to ensure that the patient's respiratory system will receive a desired breathable atmosphere;

Providing convenient access to the patient for necessary suction and intravenous tubing and for physiological monitoring transducer leads while maintaining the aforesaid stable, supportive environment;

Providing convenient access to the patient for respiratory support devices while maintaining the aforesaid stable supportive environment;

Providing a stable supportive environment as aforesaid without any undesirable carbon dioxide buildup;

Providing protection for the patient from impact, heat loss and electric shock while maintaining the aforesaid stable supportive environment;

Providing x-ray capability while maintaining the patient in the aforesaid stable supportive environment.

The foregoing and other objects, features and advantages of the invention will become more apparent from the following detailed description, which proceeds with reference to the accompanying drawings.

BRIEF DESCRIPTION OF THE DRAWINGS

In the drawings:

FIG. 8 is a perspective view showing an environmental chamber in accordance with the invention and adapted for use in a hospital intensive care unit;

FIG. 9 is a schematic view of the apparatus of FIG. 8 when the inner pliable membrane enclosure is outside the environmental chamber;

FIG. 10 is a partial sectional view taken on line 10—10 of FIG. 4; and

FIG. 11 is a perspective view of an insert for the air intake.

DETAILED DESCRIPTION OF A PREFERRED EMBODIMENT

Environmental Chamber

Figure 1:
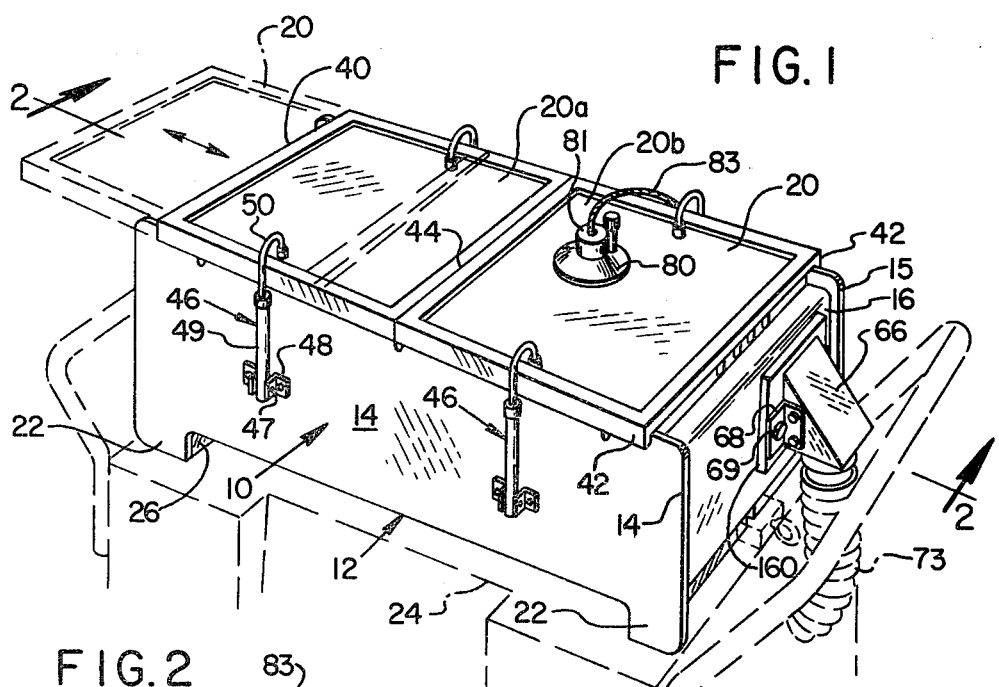
FIG. 1 is a perspective view showing an environmental chamber in accordance with the invention mounted on a mobile support platform shown in dashed lines.

Referring first to FIGS. 1-4 of the drawings, the environmental chamber 10 of the invention is formed by a rigid clear plastic outer enclosure 12 formed by flat vertical opposite sidewalls 14, 15 and opposite endwalls 16, 17 joined by a flat horizontal bottom wall 18 and a sloping top wall comprising a lid 20. These parts have been successfully made of a high-impact acrylic plastic of approximately one-quarter inch thickness, resulting in a lightweight outer enclosure weighing approximately 12 pounds suitable for receiving a small infant.

In the illustrated embodiment the "head" endwall 17 extends upwardly from the bottom wall to a greater height than the "foot" endwall 16. The upper edges of the sidewalls are straight and decline from the head endwall to the foot endwall. Thus the top wall or lid 20 slopes downwardly from the head end to the foot end of the outer enclosure. This tapered configuration allows ample working room for the doctor or nurse at the head end of the chamber while at the same time reducing the chamber space at the foot end to effect some weight savings.

Figure 2:
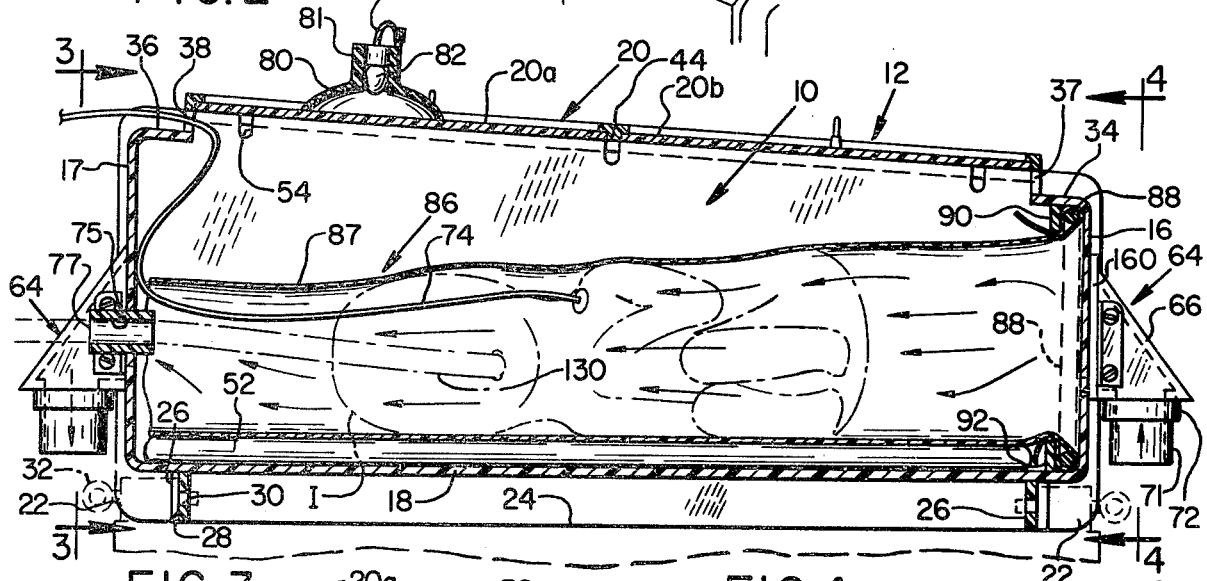
FIG. 2 is a vertical sectional view taken along the line 2—2 of FIG. 1 showing internal details of the environmental chamber including its inner pliable membrane enclosure.

Lower opposite end portions of sidewalls 14, 15 extend downwardly beyond bottom wall 18 to define short leg portions 22 at the lower four corners of the outer enclosure. The legs support the environmental chamber at an elevation above a supporting platform 24. The space thus provided between bottom wall 18 and the top surface of support platform 24 is sufficient to receive an x-ray film cassette. Thus the infant can be x-rayed while in the chamber by an overhead x-ray transmitter aimed through the lid. The platform may be either a portable self-contained life support platform equipped with all necessary life-support and monitoring components for use in ambulances or aircraft or an in-hospital mobile or stationary platform. Each laterally opposed pair of legs 22 is joined by a transverse reinforcing flange 26 which forms part of the leg structure. Each flange 26 has a vertically extending channel 28 in its outer surface midway between its ends. A pin-receiving hole 30 extends through each flange from the bottom of its channel 28 to serve as part of a quick latching means which includes a spring-biased latching pin 32 on the platform. When pin 32 and hole 30 are aligned, the pin projects into the hole to latch the environmental chamber enclosure to platform 24, as shown in FIG. 2.

The upper end portions of the opposite endwalls 16, 17 curve inwardly from the vertical to the generally horizontal to form short top wall portions 34, 36 which extend upwardly at their inner ends to terminate in short vertical flange portions 37, 38. The upper edges of such flange portions lie in the same plane as the upper edges of oppsite sidewalls 14, 15 to help support lid 20 and define the bounds of the top opening of the outer enclosure when the lid is removed.

The lid itself is designed to slide to various open or partially open positions along and guided by the top edges of opposite sidewalls 14, 15 with such top edges serving as slideways. For this purpose the clear plastic lid material is set in a lightweight opaque plastic frame 40, the opposite side edges of which form downwardly extending lips 42 which overlap the top edges of opposite sidewalls 14, 15 to help retain and guide the lid in its sliding movement. No such lip is formed on the frame portions 40 at the opposite ends of the lid, thereby enabling the lid to be slid to various open positions from either end of the outer enclosure.

In the preferred embodiment shown, lid 20 is a two-piece lid including similar square lid sections 20a, 20b. Such two-piece construction enables the lid sections 20a, 20b to be slidingly separated along their transverse parting line 44 at the center of the outer enclosure thereby providing a variable sized top access opening into the chamber from the midportion as well as from the opposite ends of the enclosure.

The lid sections are held in place against the top edges of the sidewalls while at rest or while sliding by lid-retaining clamping means 46 shown in FIG. 1. There are two such opposed clamps 46 attached to opposite sidewall 14, 15 for each lid section. Each clamp 46 is pivoted at 47 to angle brackets 48 which attach the clamp to a sidewall. A cylindrical body portion 49 of each clamp houses a spring (not shown) which biases a hook-shaped clamping portion 50 downwardly in engagement against the top surface of the lid. The lid-engaging tip of the clamping portion is preferably capped with a nonabrasive, low-friction plastic so as not to scratch the lid or impede its sliding movement. The clamps enable each lid section to be slid along the top edges of the opposite sidewalls while still being retained in abutment with such top edges. To enable removal of the lid sections from the outer enclosure, the hook portions of the clamps are simply lifted from engagement with and swung outwardly away from the lid sections.

A mattress 52 is placed along the inside bottom wall of the outer enclosure. Such mattress is preferably of a soft resilient plastic material such as Kydex brand plastic, which is x-ray transmissive and has a low heat conductivity for minimizing conductive heat loss from the infant. If desired, the mattress may have strands of small diameter nylon cord (not shown) attached to its opposite side edges at the ends and midpoint of the mattress. Each cord strand can be knotted at short intervals of one inch or so along its length and used to elevate the mattress to various levels or slopes within the environmental chamber simply by passing selected strands through notches 54 provided at three spaced positions along the top edges of the opposite sidewalls 14, 15 and hitching a selected knot in the cord against the outside of its corresponding notch to hold the strand and its connected portion of the mattress in an elevated position within the chamber. Alternatively, notches 54 may be used as access ports for passing tubing for fluids or wire leads for monitoring transducers into the chamber.

The opposite endwalls 16, 17 are also provided with similar notches 56, 58 along the top edges of vertical flange portions 37, 38. These also serve as access ports for intravenous and suction tubing (the larger notches 58) and wire leads 74 for pulse, body temperature, electrocardiogram and other physiological monitoring transducers (the smaller notches 56). The use of one such endwall notch for this purpose is illustrated, for example, in FIG. 2. These sidewall and endwall notches are sufficiently deep to prevent tubing and monitoring leads passing therethrough from obstructing the closure and sliding movement of lid sections 20a, 20b.

Figure 3:
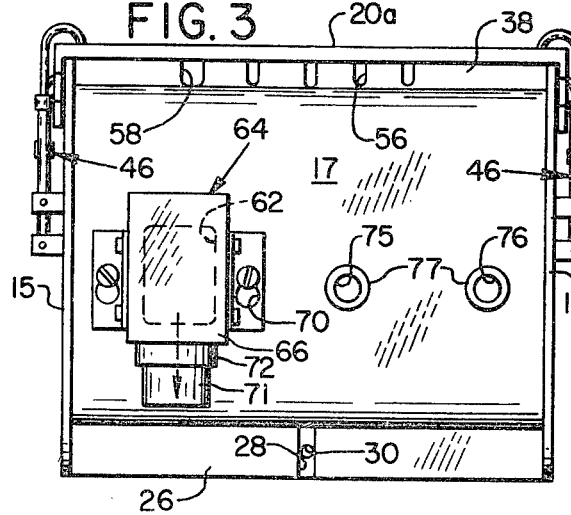
FIG. 3 is an end view of one end of the environmental chamber as viewed along the line 3—3 of FIG. 2.
Figure 4:
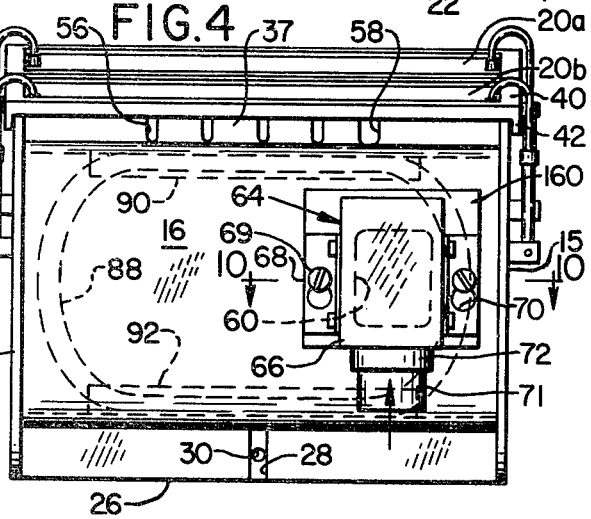
FIG. 4 is an end view of the opposite end of the environmental chamber as viewed along the line 4—4 of FIG. 2.
Figure 5:
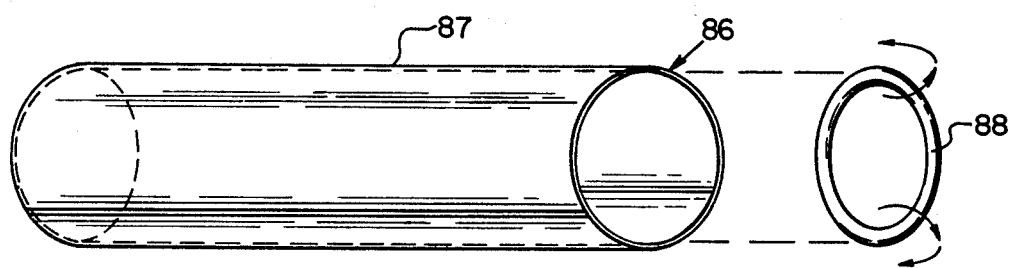
FIG. 5 is a view of the two separated elements of the inner pliable membrane enclosure of the invention shown detached from the environmental chamber.

Each opposite endwall 16, 17, as shown most clearly in FIGS. 3 and 4, has a large opening 60, 62, one for the intake and the other for the exhaust of breathable gas from the environmental chamber. A hose coupling means 64 is connected to the outside of each endwall at its opening for coupling an air-oxygen hose to the outer enclosure for communication with the chamber. Each such hose coupling means includes a generally triangular-shaped hood portion 66 connected to the outside of the endwall by angle brackets 68 and screws 69. The screws extend through keyhole shaped openings 70 in the angle brackets, shown in FIGS. 4 and 5, for quick attachment of the hose coupling assembly to its endwall. A short hose coupling tube 71 with enlarged annular boss 72 extends downwardly from hood portion 66 for receiving the end of an air-oxygen hose 73 in the manner shown in FIG. 1.

FIGS. 10 and 11 illustrate an insert 160 adapted for use in intake opening 60. Insert 160 is made of acrylic plastic and includes an air opening 161 in which are mounted anodized aluminum vanes 162, 163 for dividing the flow through the opening into three vertically oriented layers, as will be hereinafter more fully described. In the illustrated position of opening 60, vane 162 is preferably mounted at a 60° angle to endwall 16, vane 163 at a 45° angle. Positioning the vanes in this manner gives a desired distribution of the airflow.

The head endwall 17, shown best in FIGS. 2 and 3, also has two additional gas access ports 75, 76 provided with standard tube couplers 77 for providing auxiliary access to the chamber for air-oxygen tubing of respiratory assistance devices such as those used for maintaining a continuous positive airway pressure (C-PAP) in an infant. Conventional plugs (not shown) are available for plugging these auxiliary gas ports if desired when not in use.

Because the environmental chamber is designed to be used in ground transport vehicles and aircraft, at night as well as during daylight hours, special illumination means are provided for illuminating the chamber at night without casting light into the vehicle that would interfere with driver visibility. Such illumination means includes a suction cup 80 having a tubular stem portion 81 within which a small electric lamp 82 is mounted so that the bulb portion of the lamp projects into the interior of the suction cup portion. The necessary electrical conductor 83 extends from the base of the lamp out the rear of stem 81 to a source of electricity. The suction cup 80 thus serves the dual function of an attachment means for selectively attaching the illumination device to any outer wall surface of the outer enclosure and as a shade for the lamp which directs light rays only into the interior of the enclosure.

When the environmental chamber is for use in-hospital, it may be provided with a surgical light 170 and an infra-red heating light 171. Light 171 is mounted on a stanchion 172 pivotally and vertically adjustably supported by a frame 173 which is itself mounted on a support 174, as shown in FIG. 8. Infra-red heating light 171 is provided with a control box 175 including a circuit breaker. Control box 175 desirably provides control for light 171 from zero to 70% of its capacity.

Inner Pliable Membrane Enclosure

An important feature of the invention is the inner pliable membrane enclosure 86, shown in FIGS. 2, 5, 6 and 7. It is used in conjunction with the environmental chamber either within the chamber or outside the chamber in manners to be described. The inner membrane enclosure comprises two parts: A tubular clear plastic membrane 87 and a resilient deformable ring 88.

Tubular membrane 87 is attached to the shorter foot endwall 16 of the outer enclosure in surrounding relationship to gas intake opening 60 in the manner shown in FIG. 2. One open end of tubular membrane 87 is first wrapped around ring 88. Then the ring is deformed to a horizontally oblong shape as shown in FIG. 4 and inserted into upper and lower channels formed between endwall 16 and upper and lower flanges 90, 92. Upper flange 90 extends downwardly from top wall portion 34, and lower flange 92 extends upwardly from bottom wall 18. The tendency for ring 88 to spring back to its original circular shape holds it within the channels and retains an end portion of tubular membrane 87 wrapped around the ring in an open condition adjacent to endwall 16.

The opposite end of tubular membrane 87 remains free of but adjacent to opposite endwall 17 of the outer enclosure, thereby providing the physician with access to an infant within the tubular membrane as shown in FIG. 2. The free end of the tubular membrane also provides access to the infant for tubing and physiological monitoring leads in the manner shown in FIG. 2.

Use of Inner Membrane Enclosure

Figure 7:
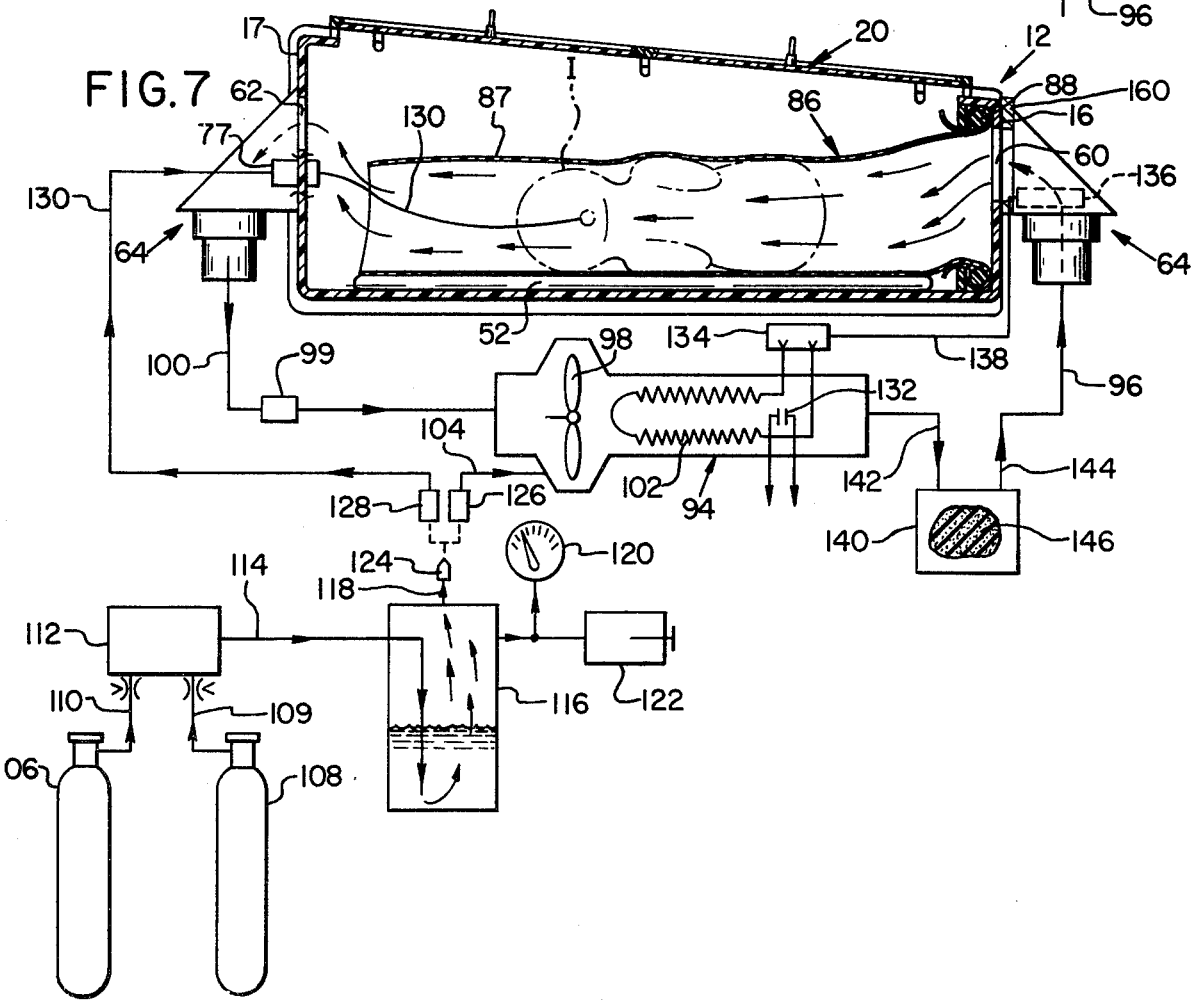
FIG. 7 is a schematic diagram illustrating use of the inner pliable membrane enclosure inside of the environmental chamber with such chamber shown as part of an air-oxygen circulation system for maintaining a desired atmosphere within the chamber and inner enclosure.

With the infant in the tubular enclosure, and the tubular enclosure within the chamber as shown in FIGS. 2 and 7, an air-oxygen mix enters such enclosure through intake opening 60 from which it flows through the length of the membrane over the infant from its feet towards its head. The gas then passes from the free end of the inner enclosure into the outer enclosure. The bulk of the gas flow passes from the outer enclosure through exhaust opening 62 at head endwall 17. However, some will also pass from the outer enclosure through top edge notches 54, 56, 58 and gas ports 75, 76 if not plugged. If the intake and exhaust openings 60, 62 are connected in a "closed" air-oxygen circuit, carbon dioxide buildup in the membrane enclosure and chamber is prevented because it is continuously flushed by the circulating air-oxygen mixture from the free end of the tubular inner membrane into the larger volume of the chamber. The carbon dioxide dissipates from there through the upper edge notches and other incidental openings in the outer enclosure to the ambient atmosphere.

When the inner membrane enclosure is used within the chamber, a heated insulated air space is created between the inner enclosure and the outer enclosure, thereby reducing what might otherwise be a substantial temperature gradient between the inner and outer surfaces of the membrane enclosure. Thus the inner surface of the membrane enclosure can be maintained at about the same temperature as the air-oxygen mixture passing through the tubular enclosure. As a result, the possibility of heat loss from the infant through radiation is reduced substantially because radiation heat loss is a function of the difference between the surface temperature of the radiating body (the infant) and the temperature of the radiation-receiving surface (the inner surface of the inner membrane), and there will be little difference between the temperatures of these two surfaces. However, without the use of the inner tubular membrane, heat loss from the infant through radiation can be substantial because of the cooling effect that the normally much colder ambient room atmosphere has on the inner surface of the outer enclosure.

Another advantage of the use of the inner enclosure is that it channels the air-oxygen mixture at a desired laminar flow rate and in a desired direction of circulation over the infant. This ensures that the infant will receive the air-oxygen mixture in the desired proportion and at a flow rate that will minimize heat losses from the infant through evaporation and convection. Without the use of the inner membrane enclosure, it is difficult to predict what flow conditions will prevail within the outer enclosure, and the infant's respiratory system might not be exposed to the desired air-oxygen mixture because of dead air spaces created by erratic or turbulent flow conditions. Turbulent flow of the breathable gas over the infant can also accelerate the loss of body heat through evaporation and convection.

Use of the insert 160 with its vanes 162, 163 further stabilizes the laminar flow over the infant, dividing it into a plurality of vertically oriented layers. The positioning of vanes 162, 163 provides a resulting flow comprising a central system and two outer streams as shown in FIG. 10, the outer streams diverging and flowing along the sides of membrane 87.

Figure 6:
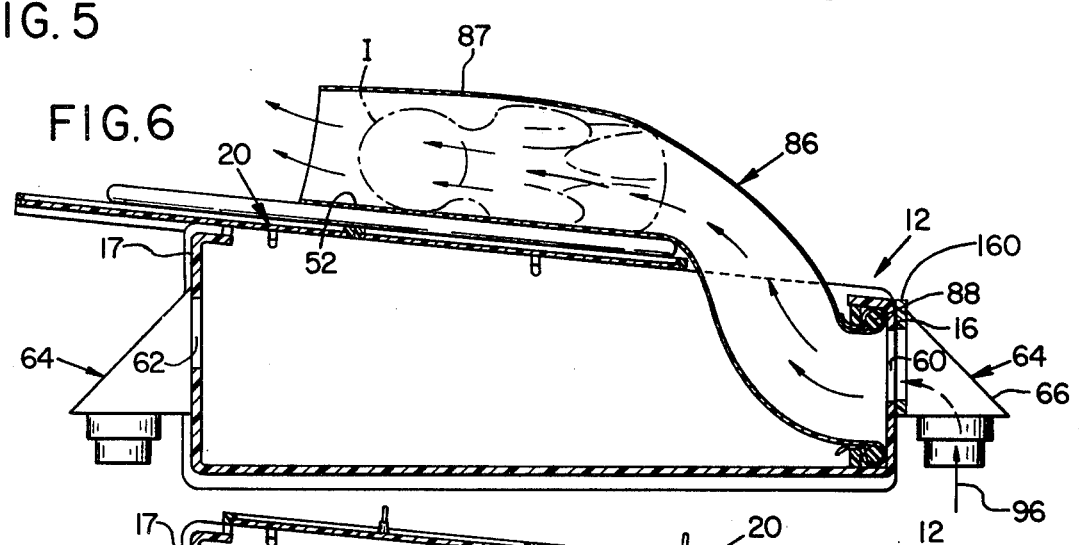
FIG. 6 is a schematic view illustrating use of the inner pliable membrane enclosure outside of the environmental chamber.

If desired, the inner membrane enclosure may also be used in the manner shown in FIG. 6 wherein the lid 20 is partially opened at the foot end of the enclosure and the tubular membrane with the infant inside supported on mattress 52 on the partially open lid. With the infant so positioned using the lid as a work table, the doctor has convenient access to the infant for administering procedures. Yet the infant still receives a desired air-oxygen mix at a desired temperature and flow rate because the heated air-oxygen mixture is still channeled into the membrane as before at the foot end of the chamber. In this use of the membrane enclosure, the air-oxygen mixture passes from the free end of the membrane to atmosphere rather than being discharged into the outer enclosure. The membrane enclosure still continues to protect the infant against radiation heat loss because its inner surface is still heated directly by the heated gas passing over such surface.

When the chamber is used in-hospital and lid 20 is partially or completely opened as shown in FIG. 8, supplemental warming of the outer surface of membrane 87 is desirable to keep it within a desired proximity of the baby's skin temperature. This is achieved with infra-red heating light 171, previously described. When lid 20 is opened, the intensity of light 171 is adjusted to eliminate any drop in the baby's body temperature. Thus, the baby is contained in an environment which is neutral from the thermal standpoint, that is, the environment is such as to minimize the infant's basil metabolic rate, whereby the infant does not experience losses due to radiant energy loss or to excessive evaporative losses. The system actually maintains the infant in a condition of positive gain from the standpoint of convective heat exchange because of the laminar flow of the large volume of approximately warmed air over his body surface. Thus, by using the infra-red heating source, the infant becomes externalized into the environment but has, in addition, a warm, humidified and appropriately oxygenated air supply passing over his body.

When the membrane enclosure is used in the manner of FIG. 6, infra-red heating light 171 may be used as shown in FIG. 9, thereby to maintain a neutral thermal environment notwithstanding the infant's further exposure atop the partially opened lid.

Air-Oxygen Circulating System

FIG. 7 illustrates schematically the inner and outer enclosures connected in a substantially closed air-oxygen circuit in accordance with the invention. Air, oxygen or an air-oxygen mixture circulates from a heater means 94 through a gas supply line 96 to the intake opening 60 at the foot end 16 of outer enclosure 12. A gas circulating means comprising an induction fan 98 within heater unit 94 induces gas flow at a desired flow rate through the outer enclosure, or though inner membrane enclosure 86 if this is used, to exhaust opening 62 of the outer enclosure. From there, the life-supporting gas returns through a filter 99 in a return line 100 to the heater unit 94 where fan 98 forces the returning gas flow over a heating element 102 before again flowing into supply line 96 for return to the intake side of the environmental chamber.

An air-oxygen mixture in the desired proportions and at the desired flow rate is supplied to the heater 94 at the induction side of fan 98 through a line 104. Air and oxygen are supplied to such line from an air tank 106 and an oxygen tank 108. The air and oxygen are led from such tanks through separate lines 109, 110 to a mixing valve 112 where the air and oxygen are mixed in a desired proportion and at desired variable flow rates and then directed through a common line 114 to a humidifier 116 where the mixture is humidified by being bubbled through water. The humidified gas mixture then flows through a line 118 and line 104 to heater 94. The discharge side of humidifier 116 has a static gas pressure gauge 120 and a high-pressure relief valve means comprising a pop-off valve 122. The pressure gauge would not be needed when using the air-oxygen circuit through the heater because the environmental chamber is not pressurized. However, it is needed when the air-oxygen mixture is optionally applied directly to the infant's respiratory system through endotracheal intubation as when administering a continuous positive airway pressure. For this purpose a separate line 130 is used, bypassing the heater and leading directly to the infant in the chamber through one of the auxiliary gas ports 75, 76 in endwall 17 of the outer enclosure.

Air-oxygen supply line 118 has a terminal end with a plug 124 which can be selectively plugged into one of two receptacles 126, 128. Receptacle 126 is connected to line 104 leading to the heater, and receptacle 128 is connected to heater bypass line 130 leading to the head end 17 of outer enclosure 12 for connection to one of the auxiliary gas port couplers 77. When the air-oxygen mixture is applied directly to the infant's respiratory system through bypass line 130, heater unit 94 circulates only heated ambient air through the outer enclosure or inner tubular membrane 87.

Typically, the heater element 102 of heater 94 includes a thermal safety switch 132 which automatically opens to de-energize the heater element, but not the fan, when circulating air temperatures reach an upper limit level. The heater also has a thermostat control 134 for controlling the temperature of the gas entering the intake opening 60 of the chamber. For this purpose a temperature sensor 136 at the intake opening senses the temperature of the gas entering the chamber and transmits temperature signals to thermostat 134 through a temperature lead 138.

An additional humidifier 140 is desirably connected into supply line 96 by lines 142, 144. Humidifier 140 includes a water saturated sponge 146 such that the gas mixture passing therethrough is stabilized to a humidity of between 55 and 60%.

Life Support Method

From the foregoing it will be apparent that the invention as described provides a unique life support method. High-risk newborn infants and other patients can be maintained and transported in a controlled, stable, life-supportive environment while at rest and during medical and surgical procedures. This is done by enclosing the patient in a flexible transparent membrane open at both ends while delivering a continuous flow of a life-sustaining gas to such person through one open end of the membrane, thereby forcing the gas to flow over the patient within the membrane and discharging it from the opposite open end of the membrane. The gas is preferably heated to a desired temperature before entering the membrane enclosure. This not only supplies external heat to the patient but also heats the inner surface of the membrane, thereby reducing loss of body heat by radiation.

The patient in the inner enclosure is supported on a mattress of low conductivity to minimize heat loss through conduction. Furthermore, the flow of life-sustaining gas through the inner enclosure is controlled so as to take place at laminar flow rates which are sufficiently low to minimize loss of body heat through evaporation and convection. Moreover, the heated atmosphere circulated through the inner enclosure is preferably humidified to further reduce loss of body heat through evaporation.

For convenience the inner enclosure is preferably tubular in shape and open at both ends. The heated life-supporting atmosphere is admitted at the foot end of the enclosure so that the slight, usually about 2° to 3° F., temperature gradient across the body is from foot to head. This direction of flow also ensures that the air-oxygen mixture channeled through the membrane enclosure will be directed toward the nostril openings of the patient for access to its respiratory system.

Preferably the foot end of the tubular member is connected to the outer enclosure in surrounding relationship to its gas intake opening so that all of the heated atmosphere will be discharged into the tubular membrane. However, the opposite, head end of the membrane remains disconnected from the outer enclosure so that the heated air-oxygen mixture and gases exhaled from the patient within the inner enclosure are discharged into ambient atmosphere or the larger outer enclosure to dissipate exhaled carbon dioxide.

Preferably the membrane enclosure is placed within the environmental chamber formed by the outer enclosure. The heated life-supporting gas is allowed to enter such chamber from the inner membrane enclosure. Thus the outer surface of the inner membrane enclosure becomes heated to reduce the temperature gradient across the membrane, reducing radiation heat losses through the membrane to a greater extent than when either the outer enclosure or inner enclosure is used alone.

Preferably the proportion of air and oxygen in the air-oxygen mixture, the flow rate through the chamber and membrane enclosure, and the temperature of the air-oxygen mixture admitted into the inner membrane can all be varied and controlled within limits. As a result of the foregoing, the patient can be maintained in a selected stable, transportable, life-supportive environment while at rest or while being administered procedures through the free open end of the membrane enclosure.

When the invention is used in-hospital, it can maintain a neutral thermal environment for the infant by passing, in laminar flow, a relatively large volume, slow velocity air source over the infant while he is protected by the flexible plastic membrane open-ended at his head, and which air is humidified and warmed appropriately. Thus, the humidified air source minimizes evaporative heat loss, and the warming of the air results in minimizing convective heat exchange, thereby further advantaging the infant. The membrane enclosure is capable of being warmed whether the lid to the outer enclosure is on or off, warmth in the latter condition being achievable at a relatively low energy cost by the infra-red light disclosed.

Having illustrated and described the principles of my invention by what is presently a preferred embodiment thereof, it should be apparent to those persons skilled in the art that such embodiment may be modified in procedures, arrangement and detail without departing from such principles. I claim as my invention all such modifications as come within the true spirit and scope of the following claims.

I claim:

1. A method of maintaining high-risk infants and other medical patients in a controlled environment while at rest and during medical procedures comprising:
   enclosing the patient in a thin elongated flexible impervious transparent tubular membrane enclosure means adapted to closely enclose the patient full length while recumbent and being open at both ends thereof, and
   delivering a continuous flow of a life-sustaining gas to said patient through one open end of said membrane to cause said gas to pass through the interior of said membrane and out the opposite end,
   said gas being divided into a plurality of vertically oriented layers as it is delivered through said one open end.

2. The method of claim 1 in which said layers comprise a central stream and two outer streams which flow along the sides of said membrane.

3. A method of maintaining high-risk infants and other medical patients in a controlled environment while at rest and during medical procedures comprising:
   enclosing the patient in a thin elongated flexible impervious transparent tubular membrane enclosure means adapted to closely enclose the patient full length while recumbent and being open at both ends thereof,
   delivering a continuous flow of a life-sustaining gas to said patient through one open end of said membrane to cause said gas to pass through the interior of said membrane and out the opposite end, and
   heating the outer surface of said membrane by infra-red heating.

4. A device for maintaining high-risk infants and other medical patients in a controlled environment while at rest and during medical procedures comprising:
   a thin elongated flexible impervious transparent tubular membrane enclosure means adapted to closely enclose the patient full length while recumbent;
   said tubular membrane being open at its opposite ends to enable maintenance of a continuous flow of a life-sustaining gas through the interior of said tubular membrane enclosure from one open end thereof to the other;
   a rigid outer enclosure defining an environmental chamber for receiving said membrane enclosure and a patient enclosed therein, said outer enclosure including a closable top access opening and an end wall portion having a gas intake opening;
   a plurality of vertically oriented vanes positioned in said gas intake opening; and
   means for attaching one open end of said tubular membrane enclosure to said end wall portion in surrounding relationship to said gas intake opening, whereby said life-sustaining gas can be supplied to said membrane enclosure in vertically oriented layers.

5. An environmental chamber for high-risk infants and other medical patients comprising:
   a rigid enclosure including flat opposite end and side walls, a flat bottom wall and a flat, removable lid, all defining said chamber, said chamber being of sufficient size to enclose said patient,
   said walls being composed of a clear electrically insulative, but x-ray transmissive material,
   said lid being slidable on upper edges of said opposite side walls to variable open positions from either end wall of said enclosure,
   spring-biased clamping means on said opposite side walls for retaining said lid against the upper edges of said side walls while enabling sliding movement of said lid therealong to its variable open positions,
   infra-red heating means disposed above said enclosure for providing heat to said patient when said lid is in an open position,
   means defining a gas intake opening in one end wall and a gas exhaust opening in an opposite end wall for the intake and exhaust of a life-sustaining gas from said chamber,
   a supporting platform for said rigid enclosure,
   leg means extending downwardly from the opposite ends of said bottom wall of said rigid enclosure for elevating said bottom wall above said supporting platform to provide access for x-ray film below said bottom wall and electrical and thermal isolation of said enclosure from said supporting platform, and
   latching means on said leg means for selective attachment of said enclosure to said supporting platform,
   and a thin elongated flexible impervious transparent tubular membrane enclosure means adapted to closely enclose the patient full length while recumbent and being open at its opposite ends, said membrane enclosure means being removably attached to said rigid enclosure at said one end wall in surrounding relation to said gas intake opening, said membrane enclosure means while attached to said end wall being usable within said enclosure and on said lid.

6. A device for maintaining high-risk infants and other medical patients in a controlled environment while at rest and during medical procedures comprising:
   a thin elongated flexible impervious transparent tubular membrane enclosure means adapted to closely enclose the patient full length while recumbent,
   said tubular membrane being open at its opposite ends to enable maintenance of a continuous flow of a life-sustaining gas through the interior of said tubular membrane enclosure from one open end thereof to the other;
   a rigid outer enclosure defining an environmental chamber for receiving said membrane enclosure and a patient enclosed therein, said outer enclosure including a closable top access opening and two opposite end wall portions, one of said end wall portions having a gas intake opening and the other of said end wall portions having a gas exhaust opening,
   said intake and exhaust openings including hose coupling means for coupling gas supply and gas return hoses to said opposite end wall portions;
   a gas supply and a gas return conduit connected respectively to said gas intake and gas exhaust openings;
   means for attaching one open end of said tubular membrane enclosure to said one end wall portion in surrounding relationship to said gas intake opening, whereby said life-sustaining gas can be supplied to said membrane enclosure;

gas circulating means connected to said gas supply and return conduits for providing a positive gas circulation through said conduits, said outer enclosure and said tubular membrane enclosure; and humidifying means connected to said gas supply conduit for humidifying gas supplied to said membrane enclosure.

7. A device for maintaining high-risk infants and other medical patients in a controlled environment while at rest and during medical procedures comprising:

a thin elongated flexible impervious transparent tubular membrane enclosure means adapted to closely enclose the patient full length while recumbent and being open at its opposite ends, means for connecting one open end of said membrane enclosure means to a source of life-sustaining gas, an infra-red heating means disposed adjacent but in spaced relation to said membrane and being directed toward said membrane so as to be operable to provide radiant heat energy to the interior of said membrane.

8. Apparatus according to claim 7, including a rigid outer enclosure defining an environmental chamber for receiving said membrane enclosure means with a patient enclosed therein, said outer enclosure including a closable top access opening and an end wall portion having a gas intake opening, said means for connecting one open end of said membrane enclosure means to a source of life-sustaining gas, including means operable to connect said one open end to said end wall portion in surrounding relation to said gas intake opening.

* * * * *